US011474173B2

(12) United States Patent
Vester et al.

(10) Patent No.: US 11,474,173 B2
(45) Date of Patent: Oct. 18, 2022

(54) MAGNETIC RESONANCE APPARATUS AND METHOD FOR OPERATING A MAGNETIC RESONANCE APPARATUS, COMPUTER PROGRAM AND ELECTRONICALLY READABLE DATA STORAGE MEDIUM

(71) Applicant: Siemens Healthcare GmbH, Erlangen (DE)

(72) Inventors: Markus Vester, Nuremberg (DE); Carmel Hayes, Munich (DE); Stefan Popescu, Erlangen (DE); Mathias Blasche, Buckenhof (DE); Matthias Gebhardt, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/130,347

(22) Filed: Dec. 22, 2020

(65) Prior Publication Data

US 2021/0208219 A1 Jul. 8, 2021

(30) Foreign Application Priority Data

Jan. 3, 2020 (DE) ...................... 10 2020 200 013.1

(51) Int. Cl.
*G01R 33/34* (2006.01)
*A61B 5/00* (2006.01)

(52) U.S. Cl.
CPC ...... *G01R 33/34061* (2013.01); *A61B 5/0006* (2013.01); *G01R 33/34023* (2013.01)

(58) Field of Classification Search
CPC ........ G01R 33/34061; G01R 33/34023; A61B 5/0006
See application file for complete search history.

(56) References Cited

U.S. PATENT DOCUMENTS 5,867,027 A * 2/1999 Kawamoto ........ G01R 33/4215
324/318
6,157,194 A * 12/2000 Vassallo ................. G01R 33/54
324/322

(Continued)

FOREIGN PATENT DOCUMENTS

DE 60225515 T2 4/2009
EP 3467531 A1 4/2019

OTHER PUBLICATIONS

Cincinnati Children's; "MRIAirway (sleep) Study" 2015.*

(Continued)

*Primary Examiner* — Dixomara Vargas
(74) *Attorney, Agent, or Firm* — Harness, Dickey & Pierce, P.L.C.

(57) ABSTRACT

A magnetic resonance apparatus, for acquiring magnetic resonance data from a person who is asleep, includes a person support apparatus to provide a sleeping place; an acquisition arrangement including a radiofrequency coil arrangement for transmitting excitation pulses and for receiving magnetic resonance signals; and a controller, designed to operate the acquisition arrangement according to a magnetic resonance sequence for acquiring a magnetic resonance dataset from a region under examination of the person. The magnetic resonance apparatus includes a main magnetic field of strength less than 20 mT, in particular less than 10 mT, and the controller includes an acquisition unit for acquiring a magnetic resonance dataset via a prolonged magnetic resonance sequence having a total acquisition duration of more than one hour.

26 Claims, 4 Drawing Sheets

(56) References Cited

U.S. PATENT DOCUMENTS

| | | | | |
|---|---|---|---|---|
| 6,466,812 | B1* | 10/2002 | Overweg | G01R 33/381 324/309 |
| 9,489,854 | B2* | 11/2016 | Haruta | A61B 5/4088 |
| 10,267,886 | B2 | 4/2019 | Bernstein et al. | |
| 10,302,731 | B2 | 5/2019 | Trzasko et al. | |
| 2003/0074033 | A1* | 4/2003 | Pless | G16H 40/60 607/48 |
| 2003/0076205 | A1 | 4/2003 | Wang et al. | |
| 2004/0083257 | A1* | 4/2004 | Gortler | G16H 10/60 709/201 |
| 2005/0258832 | A1* | 11/2005 | Eberlein | G01R 33/385 324/318 |
| 2006/0127313 | A1* | 6/2006 | Goldman | A61K 49/10 424/9.3 |
| 2007/0055538 | A1* | 3/2007 | Burton | G06F 21/32 705/2 |
| 2008/0265890 | A1* | 10/2008 | Graesslin | G01R 33/3635 324/318 |
| 2009/0222987 | A1* | 9/2009 | He | A61B 5/055 5/601 |
| 2013/0225979 | A1* | 8/2013 | Borgert | A61K 49/1818 600/420 |
| 2014/0111202 | A1* | 4/2014 | Wald | G01R 33/383 324/309 |
| 2015/0028873 | A1* | 1/2015 | Dohata | G01R 33/385 324/322 |
| 2015/0054503 | A1* | 2/2015 | Chen | G01R 33/4831 324/303 |
| 2015/0091567 | A1* | 4/2015 | Grodzki | G01R 33/4822 324/309 |
| 2015/0177343 | A1* | 6/2015 | Wald | A61B 5/0042 324/309 |
| 2015/0241531 | A1* | 8/2015 | Liu | G01R 33/50 324/309 |
| 2016/0054414 | A1* | 2/2016 | Haider | G01R 33/546 324/322 |
| 2016/0069968 | A1* | 3/2016 | Rothberg | G01R 33/3858 324/322 |
| 2016/0069976 | A1* | 3/2016 | Kickhefel | G01R 33/4828 324/309 |
| 2016/0077175 | A1* | 3/2016 | Mori | G01R 33/307 324/321 |
| 2017/0003365 | A1* | 1/2017 | Rosen | G01R 33/445 |
| 2017/0160365 | A1* | 6/2017 | Helle | G01R 33/56366 |
| 2017/0160366 | A1* | 6/2017 | Tisdale | G01R 33/5613 |
| 2017/0219672 | A1* | 8/2017 | Miyazaki | G01R 33/5635 |
| 2017/0322276 | A1* | 11/2017 | Bhat | G01R 33/4828 |
| 2018/0067176 | A1* | 3/2018 | Weingartner | G01R 33/385 |
| 2018/0217217 | A1 | 8/2018 | Weingartner et al. | |
| 2018/0217220 | A1* | 8/2018 | Gulani | G01R 33/5676 |
| 2018/0231626 | A1* | 8/2018 | Gulani | G01R 33/4824 |
| 2018/0314490 | A1* | 11/2018 | Lee | G06F 40/30 |
| 2018/0374213 | A1* | 12/2018 | Arnold | G06N 3/049 |
| 2019/0000406 | A1* | 1/2019 | Liu | G01T 1/2018 |
| 2019/0107590 | A1* | 4/2019 | Fukushima | G01N 24/081 |
| 2019/0128982 | A1* | 5/2019 | Wald | G01R 33/4822 |
| 2019/0128986 | A1* | 5/2019 | Helle | G01R 33/56366 |
| 2019/0257903 | A1* | 8/2019 | Poole | G01R 33/389 |
| 2019/0346524 | A1* | 11/2019 | Helle | G01R 33/5608 |
| 2020/0249292 | A1 | 8/2020 | Biber et al. | |
| 2020/0294286 | A1* | 9/2020 | Helle | G06T 7/0012 |

OTHER PUBLICATIONS

American Cancer Society; "MRI for Cancer"; 2019.*
John Hopkins Medicine; "Health Magnetic Resoance Imaging (MRI) of the Spine and Brain" ; 2022.*
Debra Sullivan et al. ; "MRI duration by Type of Scan"; 2005-2022.*
Mayo Clinic; "MRI"; 1998-2022.*
Yoshida, K. et al:; "Evaluation of sleep apnea syndrome with low-field magentic resonance fluoroscopy"; European Radiology; vol. 9; pp. 1197-1202; ISSN 1432-1084; 1999.
Kartäusch, Ralf et al.: "Spatial phase encoding exploiting the Bloch-Siegert shift effect"; in:Magnetic Resonance Materials in Physics, Biology and Medicine; vol. 26; No. 5; 2013; DOI: 10.1007/s10334-013-0417-0; 2013.
Sarracanie, Mathieu et al:; "Low-Cost High-Performance MRI"; Nature Scientifc Reports 5; ISSN 2045-2322; DOI: 10.1038/srep15177; 2015.
Fronsac, Freiburg GradLoc, Yale O-space.
Arterial Spin-Labeling in Routine Clinical Practice, Part: Technique and Artefacts, A.R. Deibler et al.; A.R. Deibler et al., Arterial Spin-Labeling in Routine Clinical Practice, Part: Technique and Artefacts, DOE 10.3174/ajnr.A1030, Aug. 2008, pp. 1228-1234.
Littin, S. et al.,"Optimization of a planar gradient system for imaging with non-linear gradients", ESMRMB 2011, pp. 371-372, EPOS Posters 529.
Halse, M. et al., "A practical and flexible implementation of 3D MRI in the Earth's magnetic field", Journal of Magnetic Resonance 182, pp. 75-83, 2006.
Sharp, J. et al., „MRI Using Radiofrequency Magnetic Field Phase Gradients, Magnetic Resonance in Medicine 63, pp. 151-161, 2010.
German Search Report for German Patent Application No. 102020200013.1 dated Nov. 16, 2020.

* cited by examiner

MAGNETIC RESONANCE APPARATUS AND METHOD FOR OPERATING A MAGNETIC RESONANCE APPARATUS, COMPUTER PROGRAM AND ELECTRONICALLY READABLE DATA STORAGE MEDIUM

PRIORITY STATEMENT

The present application hereby claims priority under 35 U.S.C. § 119 to German patent application number DE 102020200013.1 filed Jan. 3, 2020, the entire contents of which are hereby incorporated herein by reference.

FIELD

Example embodiments of the application generally relate to a magnetic resonance apparatus for acquiring magnetic resonance data from a person who is asleep, comprising a person support apparatus, which provides a sleeping place, an acquisition arrangement, which comprises a radiofrequency coil arrangement for transmitting excitation pulses and for receiving magnetic resonance signals, and a controller, which is designed to operate the acquisition arrangement according to a magnetic resonance sequence for acquiring a magnetic resonance dataset from a region under examination of the person. Example embodiments of the application also relate to a method for operating the magnetic resonance apparatus, to a computer program and to an electronically readable data storage medium.

BACKGROUND

Magnetic resonance imaging has become established in the medical sector, in particular in the field of medical diagnostics. It involves using clinical magnetic resonance apparatuses that usually employ extremely high fields, for instance in the range of 0.5-10 T, to ensure not only especially high image quality or generally magnetic resonance data quality but also a fast examination process. This is because, for financial and practical reasons, such magnetic resonance apparatuses, which may be provided in clinics and/or radiology centers, for instance, are available to patients only for a certain length of time, for instance 20 minutes. All the necessary examinations must be carried out in this time frame. Magnetic resonance apparatuses are large, heavy pieces of equipment which are costly to install, for instance involving implementing a shielded cabin in a clinic/radiology center. More widespread use of magnetic resonance diagnostics, however, could generate a large amount of valuable information.

SUMMARY

At least one embodiment of the invention is directed to a magnetic resonance apparatus that is available for more frequent and more prolonged use.

Embodiments of the invention are directed to a magnetic resonance apparatus, a method, a computer program and an electronically readable data storage medium as claimed in the independent claims. The claims contain advantageous embodiments.

For a magnetic resonance apparatus according to an embodiment of the present invention, the magnetic resonance apparatus has a main magnetic field of strength less than 20 mT, in particular less than 10 mT, and the controller comprises an acquisition unit for acquiring a magnetic resonance dataset by way of a prolonged magnetic resonance sequence having a total acquisition duration of more than one hour. The controller controls at least the acquisition arrangement to implement the particular magnetic resonance sequence, in particular the prolonged magnetic resonance sequence.

An embodiment of the present invention also relates, in addition to the magnetic resonance apparatus, to a method for operating a magnetic resonance apparatus according to an embodiment of the invention, in which method the at least one prolonged magnetic resonance sequence is used to acquire at least one magnetic resonance dataset from a person sleeping on the sleeping place. All the statements relating to the magnetic resonance apparatus according to an embodiment of the invention can also be applied analogously to the method according to the invention, and therefore the advantages already described can also be achieved by the method. In addition, in particular different functionalities of the controller can also be interpreted as method steps, for instance performing motion correction and/or motion cleansing, and/or triggering specific magnetic resonance sequences or parameterizing the sequences, in particular based upon the person-related data.

A computer program according to an embodiment of the invention can be loaded, for example, directly into a memory of a controller of a magnetic resonance apparatus according to an embodiment of the invention, and comprises program segments to perform the steps of a method according to the invention when the computer program is executed in the controller of the magnetic resonance apparatus. The computer program can be stored on an electronically readable data storage medium according to an embodiment of the invention, which therefore comprises electronically readable control information stored thereon that comprises at least one the computer program and is designed such that it performs a method according to an embodiment of the invention when the data storage medium is used in a controller of a magnetic resonance apparatus according to an embodiment of the invention. The data storage medium may be in particular a non-transient data storage medium, for instance a CD-ROM.

A magnetic resonance apparatus according to an embodiment of the invention is for acquiring magnetic resonance data from a person who is asleep, comprising:
  a person support apparatus, to provide a sleeping place;
  an acquisition arrangement, including a radiofrequency coil arrangement to transmit excitation pulses and to receive magnetic resonance signals; and
  a controller, designed to operate the acquisition arrangement according to a magnetic resonance sequence for acquiring a magnetic resonance dataset from a region under examination of the person, and the controller including:
    an acquisition unit to acquire a magnetic resonance dataset by way of a prolonged magnetic resonance sequence having a total acquisition duration of more than one hour,
  wherein, the magnetic resonance apparatus has a main magnetic field of strength less than 20 mT.

A method according to an embodiment of the invention is for operating a magnetic resonance apparatus including a person support apparatus, to provide a sleeping place; an acquisition arrangement, including a radiofrequency coil arrangement to transmit excitation pulses and to receive magnetic resonance signals; and a controller, designed to operate the acquisition arrangement according to a magnetic resonance sequence for acquiring a magnetic resonance dataset from a region under examination of the person, and the controller including an acquisition unit to acquire a magnetic resonance dataset by way of a prolonged magnetic resonance sequence having a total acquisition duration of more than one hour, wherein the magnetic resonance apparatus has a main magnetic field of strength less than 20 mT, the method comprising:

using at least one prolonged magnetic resonance sequence to acquire at least one magnetic resonance dataset from the person sleeping on the sleeping place of the person support apparatus.

A non-transitory computer readable medium according to an embodiment of the invention is for storing a computer program, to perform the method of an embodiment when the computer program is executed in a controller of a magnetic resonance apparatus.

BRIEF DESCRIPTION OF THE DRAWINGS

Further advantages and details of the present invention are presented in the example embodiments described below and with reference to the drawing, in which.

DETAILED DESCRIPTION OF THE EXAMPLE EMBODIMENTS

Figure 1:
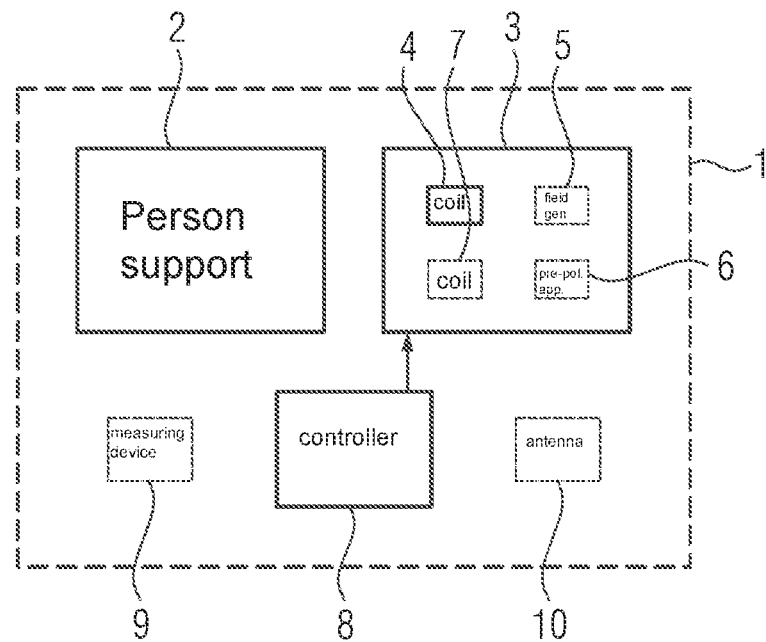
FIG. 1 shows the fundamental components of a magnetic resonance apparatus according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code.

Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

For a magnetic resonance apparatus according to an embodiment of the present invention, the magnetic resonance apparatus has a main magnetic field of strength less than 20 mT, in particular less than 10 mT, and the controller comprises an acquisition unit for acquiring a magnetic resonance dataset by way of a prolonged magnetic resonance sequence having a total acquisition duration of more than one hour. The controller controls at least the acquisition arrangement to implement the particular magnetic resonance sequence, in particular the prolonged magnetic resonance sequence.

An aim of at least one embodiment of the present invention is to resolve the conflict between today's centrally located diagnostic magnetic resonance apparatuses and the trend towards decentralized health care (home health care). A magnetic resonance apparatus is therefore proposed that is designed such that it can be used by one person continuously over many hours during the overnight sleeping period. In other words, this departs from the current magnetic resonance imaging paradigm of acquiring the maximum possible amount of magnetic resonance data from the patient as quickly as possible, to a model in which magnetic resonance imaging is available to everyone, in particular in their own home, and yet allows magnetic resonance data to be acquired over a longer time frame during sleeping.

The specific implementation according to an embodiment of the invention is based on the idea of making use of the main resource available for an embodiment in the form of a home appliance, namely time, in order to compensate for options that are no longer possible for such home appliances, for instance shielding, superconducting magnets, cooling apparatuses and the like. For example it is known that the signal-to-noise ratio (SNR) is essentially inversely proportional to the main magnetic field strength of the magnetic resonance apparatus, but it also increases proportionally with the root of the total acquisition duration.

It is therefore proposed according to an embodiment of the invention to apply a far lower main magnetic field strength, namely of less than 20 mT, but instead to extend considerably, for instance by a factor of 100, the duration of magnetic resonance sequences for acquiring a magnetic resonance dataset, resulting in prolonged magnetic resonance sequences having a total acquisition duration of longer than one hour. Whereas today in diagnostic magnetic resonance systems in clinics and/or radiology centers for example only a few repetitions are acquired, in particular in the double-digit range, in the context of an embodiment of the present invention it is possible to provide, for instance, more than 1000 repetitions within a prolonged magnetic resonance sequence, so that then it is possible to improve again the signal-to-noise ratio for instance by averaging. For example, if a clinical magnetic resonance sequence has 50 repetitions and a duration of 40 s, for instance, each prolonged magnetic resonance sequence can provide a hundred-fold increase, for instance, resulting in the use of 5000 repetitions in a total acquisition duration of one hour and 7 minutes, for example.

In the present case, a magnetic resonance sequence shall be understood to mean the succession of excitation pulses and acquisition time windows that ultimately delivers a complete magnetic resonance dataset, for instance an image dataset. Thus a magnetic resonance sequence shall be understood to mean an acquisition protocol that is intended to deliver a specific magnetic resonance dataset.

It has therefore been found as part of an embodiment of the present invention that the examination time during sleep, which time is longer by orders of magnitude, allows the use of very low main magnetic field strengths. This makes it possible to create a small, lightweight and low-cost magnetic resonance system in the form of the magnetic resonance apparatus according to the invention, which can be installed, for instance, in the home of at least one person, but also in other places, for example in hospital rooms, retirement homes and the like.

The person support apparatus is preferably in the form of a comfortable bed in this case. In particular, the person support apparatus can preferably comprise a padded mattress. In addition, the person support apparatus can include a cushion and/or a blanket. Thus the person support apparatus thereby provides a sleeping place in which it is possible to fall asleep pleasantly and comfortably, in order then to acquire during the sleeping period, i.e. when a person is largely motionless, magnetic resonance datasets over longer times. It should also be mentioned at this point that in the context of an embodiment of the present invention, although not necessarily every magnetic resonance sequence used while the person is sleeping on the person support apparatus must have a total acquisition duration of over an hour, it is always the case that at least some use is made of prolonged magnetic resonance sequences having a total acquisition duration of more than one hour.

Since, according to an embodiment of the invention, the magnetic resonance data is obtained over a long time during sleep, this facilitates personal monitoring, for example patient monitoring, at home or else in a standard hospital room. For instance, this type of monitoring may relate to blood pressure and/or possible strokes.

Furthermore, another advantage of the long total acquisition duration in the magnetic resonance apparatus according to an embodiment of the invention is also that sporadically occurring physiological states of the person can be detected, for instance extra systoles. Since the person is scanned while asleep, it is also advantageous that people hardly move at all over a prolonged time during deep-sleep stages, and therefore in particular better conditions exist than those resulting from involuntary movements during a magnetic resonance examination while awake as is common today.

The use of contrast agents must be deemed problematic with the approach here of prolonged magnetic resonance acquisition processes. Magnetic resonance contrast agents, for example gadolinium-based contrast agents, work via their molecular magnetism, which results in shorter decay times for the spin magnetization in the immediately surrounding tissue, thereby increasing the T1 contrast of this tissue. Tumors can hence be identified for example. This effect, however, usually lasts only a few seconds, occasionally up to a minute. In addition, the contrast agent then becomes distributed around the body. Subsequent acquisitions have far lower contrast variations than during the first inflow.

It can thus be provided in an advantageous development of an embodiment of the invention that the controller is designed to use arterial spin labeling as a contrast-agent substitute. For the purpose of arterial spin labeling (ASL), additional radiofrequency pulses can be used, for example, to achieve spin inversion of flowing blood adjacent to a slice to be acquired. When these inverted spins flow into the slice to be acquired, the signal intensity reduces slightly but detectably, for instance it can be detected by a subtraction technique.

Other ASL techniques also exist that obviously can also be used correspondingly in the context of an embodiment of the present invention. In this regard, reference is made purely by way of example to the article by A. R. Deibler et al., "Arterial Spin-Labeling in Routine Clinical Practice, Part 1: Technique and Artifacts", American Journal of Neuroradiology (29) 2008, pages 1228-1234, the entire contents of which are hereby incorporated herein by reference. Unlike the use of contrast agents, ASL acquisitions can be performed practically continuously without a saturation effect, and are therefore suitable particularly for imaging over longer total acquisition durations during sleep.

Low-field magnetic resonance, i.e. a main magnetic field in the mT range or even in the µT range, is used in the context of an embodiment of the present invention. In particular it is even conceivable to employ Earth's magnetic-field magnetic resonance imaging in the context of an embodiment of the present invention. In other words, according to a development of an embodiment of the present invention, the magnetic resonance apparatus is designed to use the Earth's magnetic field as the main magnetic field. The strength of the Earth's magnetic field typically lies in the region of 50 µT. Numerous studies have already been carried out to prove that magnetic resonance imaging or magnetic resonance data acquisition in general is also possible using the Earth's magnetic field as the main magnetic field. It is particularly expedient in this context if a pre-polarization apparatus for aligning nuclear spins of the person before a measurement is provided as part of the acquisition arrangement.

The pre-polarization is used to increase the sensitivity of the magnetic resonance data acquisition. It involves applying a pre-polarizing field in the field of view of the magnetic resonance apparatus in order to achieve increased thermal polarization in the region under examination. After a certain time, the pre-polarizing pulse is switched off adiabatically, which results in reorientation of the nuclear spins in the direction of the Earth's magnetic field while maintaining an increased level of polarization. This increased magnetization can subsequently be manipulated by radiofrequency pulses and/or gradient pulses just as in standard clinical magnetic resonance apparatuses.

In a specific embodiment, the pre-polarization apparatus can comprise, for example, an electromagnet for generating a pre-polarizing pulse (pre-polarization pulse), which may be part of a magnetic resonance sequence, in particular also of a prolonged magnetic resonance sequence. On the subject of imaging in the Earth's magnetic field, reference is made purely by way of example to the article by Meghan E. Halse et al., "A practical and flexible implementation of 3D MRI in the Earth's magnetic field", Journal of Magnetic Resonance 182 (2006), pages 75-83, the entire contents of which are hereby incorporated herein by reference.

Additionally or alternatively, it can also be provided in the context of the invention that the magnetic resonance apparatus comprises as part of the acquisition arrangement a main-field generating apparatus for generating the main magnetic field. The fact that only extremely low fields, in particular of less than 10 mT, are meant to be used allows slim and lightweight magnet structures, and therefore the main-field generating apparatus can preferably be arranged only on one side of the person support apparatus, in particular beneath the sleeping place, and/or can comprise a Helmholtz-coil pair. Corresponding slim and lightweight magnet structures have already been proposed for low-field magnetic resonance imaging and can also be used in the context of an embodiment of the present invention.

An additional, general advantage of the magnetic resonance apparatus according to an embodiment of the invention should also be mentioned at this point. Using an extremely low main magnetic field can also significantly reduce the radiofrequency exposure of the person, which accordingly means that there is also only an extremely low SAR load.

Since it can be the case for the magnetic resonance apparatus according to an embodiment of the invention that there is increased noise, or in other words a lower signal-to-noise ratio, an embodiment of the invention can moreover also provide that the controller is designed to use at least one, in particular iterative, denoising algorithm for noise reduction in the magnetic resonance dataset. Denoising algorithms generally known in the prior art can be used here, preferably involving an iterative process.

The magnetic resonance apparatus according to an embodiment of the invention can also have an extremely quiet design thanks to the low main magnetic field and the longer timescales. In particular, the embodiment according to the invention allows the use of weak and slow main magnetic field gradients, which is also associated with low power consumption and a low sound level.

It is also particularly advantageous in this context if the controller is designed to switch a gradient before the excitation pulse in at least one magnetic resonance sequence used, in particular in the at least one prolonged magnetic resonance sequence, wherein this magnetic resonance sequence comprises no further switching operations for gradient pulses before the end of a readout period following the excitation pulse. It is conceivable particularly advantageously here that the controller is designed for radial sampling of k-space. There is a large amount of time available before the excitation pulse is output for switching the gradient more slowly, thus in particular for implementing low slew rates for the gradient pulse, thus achieving a low sound level and SAR load and low power consumption. The excitation pulse takes place only after the gradient pulse has switched, and there is no need for further, rapid gradient pulses in the far shorter wait time until the acquisition time window, especially when radial sampling of k-space is performed. In other words, there is no need for any further gradient to be switched between the transmitting and receiving by the radiofrequency coil arrangement. The load on the person can again be kept low by these devices.

In particular when a gradient coil is employed, the controller can be designed to use gradient switching times longer than 1 ms, in particular longer than 10 ms, and/or to use gradient strengths of less than 1 mT/m, in particular less than 200 µT/m. Such gradient fields can be implemented with low power consumption, at a low sound level and low SAR load.

According to a particularly advantageous embodiment of the present invention, the controller is designed to use, in particular solely, the radiofrequency coil arrangement for spatial encoding in the magnetic resonance data acquisition, in particular to use the TRASE method and/or to use a Bloch-Siegert shift gradient. Spatial encoding of this type is also referred to as spatial encoding using radiofrequency gradients. For example, an article by J. C. Sharp and S. B. King, "MRI Using Radiofrequency Magnetic Field Phase Gradients", Magnetic Resonance in Medicine 63 (2010), pages 151-161, the entire contents of which are hereby incorporated herein by reference, proposes performing spatial encoding based upon phase gradients of the radiofrequency field in order to define a silent magnetic resonance principle containing no main magnetic field gradients, which is introduced in the article as TRASE (Transmit Array Spatial Encoding). A conference paper by Ralf Kartäusch et al., "Spatial phase encoding using a Bloch-Siegert shift gradient", Proc. Intl. Soc. Mag. Reson. Med. 21 (2013), page 0371, the entire contents of which are hereby incorporated herein by reference, proposes a robust RF-only spatial-encoding method, which mimics conventional phase encoding by exploiting the properties of spatially dependent Bloch-Siegert phase shifts induced by a radiofrequency gradient coil.

Such variants can be employed with particular advantage also for the magnetic resonance apparatus according to an embodiment of the invention because not only can special gradient coils or gradient coil arrangements be omitted but also extremely quiet spatial encoding is provided that manages with a low SAR load.

If, nonetheless, spatial encoding via a gradient coil arrangement is meant to be provided, a particularly advantageous embodiment of the present invention provides that the magnetic resonance apparatus comprises as part of the acquisition arrangement a flat, in particular monoplanar, gradient coil, which is arranged only on one side of the person support apparatus, in particular beneath the sleeping place. The gradient coil is thereby in a form that as far as possible does not restrict the positioning of the patient on the sleeping place during sleep, allowing unhindered movement of the person. In particular, the view onto the patient is also unobstructed, and therefore video monitoring and/or patient pose detection can be performed at a distance, which will be discussed in greater detail below. For this purpose, it is proposed to use an in particular monoplanar, flat gradient coil, which can be provided as an integral part of the person support apparatus. A gradient coil of this type has been described, for example, in conference paper no. 529 by S. Littin et al., "Optimization of a planar gradient system for imaging with non-linear gradients", at ESMRMB 2011, cf. page 371 of the EPOSTM Posters, the entire contents of which are hereby incorporated herein by reference.

The gradient coil in this case generates orthogonal, or at least linearly independent, encoding gradient fields. Particularly advantageously, the controller is designed to correct non-linearities in the gradient field during the reconstruction. For example, an iterative image reconstruction method with built-in correction for gradient non-linearities can be used here, which method removes geometric image distortions and signal dispersion resulting from dephasing. "O-Space", FRONSAC and GradLoc are names of example procedures, and reference is also made to U.S. Pat. Nos. 10,302,731 B2 and 10,267,886 B2 in this connection, the entire contents of each of which are hereby incorporated herein by reference.

As regards the at least one radiofrequency coil of the radiofrequency coil arrangement, according to a preferred embodiment of the magnetic resonance apparatus at least one radiofrequency coil of the radiofrequency coil arrangement is arranged inside the person support apparatus, in particular inside a mattress and/or inside a pillow and/or inside a blanket, and/or inside an item of clothing that can be worn by the person. Other variants of the integration into the person support apparatus are also conceivable, for instance inside a support that carries a mattress, inside a mattress protector and the like. The relevant radiofrequency coils can be in the form of local coils or local coil elements. By placing radiofrequency coils inside the mattress and/or inside a mattress protector and/or inside a pillow and/or inside a blanket for covering the person it is possible to position the radiofrequency coils close to the person. This can improve the imaging quality while also allowing lower power consumption. It is also conceivable, but less preferable, to arrange radiofrequency coils in items of clothing, which are worn by the person while sleeping.

In a particularly advantageous development of the present invention, in addition to the gradient coil and the at least one radiofrequency coil, the main-field generating apparatus and/or the pre-polarization apparatus can also be integrated in the person support apparatus. A magnetic resonance apparatus is thereby produced that can be described as a flat-bed apparatus, for example, since no other components whatsoever of the acquisition arrangement need to be provided above the sleeping place. This results in a compact construction which allows, for example, the term magnetic resonance bed to be used to describe the magnetic resonance apparatus. It should be mentioned here that in addition to the integrative arrangement of the components of the acquisition arrangement inside the person support apparatus, preferably beneath the sleeping place, other embodiments are also conceivable in which the magnetic resonance apparatus is embodied, for example, in the manner of a four-poster bed, in which components of the acquisition arrangement that are meant to be arranged above the sleeping place can be supported, for example, by posts positioned in the corners of the sleeping area.

In addition to integrating most, in particular all, of the components of the acquisition arrangement inside the person support apparatus, it is also conceivable in the context of the present invention to integrate the controller at least in part, in particular entirely, into the person support apparatus. The magnetic resonance apparatus is then provided as a compact magnetic resonance device or magnetic resonance bed. Obviously it is also possible to provide at least parts of the controller for controlling the acquisition arrangement outside the person support apparatus.

According to a further, particularly advantageous embodiment of the present invention, the magnetic resonance apparatus comprises at least one additional measuring device, which acquires person-related data of the person. For example, the measuring device(s) may be a camera, in particular a 3D camera and/or a terahertz camera, and/or an ECG apparatus and/or a heart rate monitor and/or an oximeter. Such measuring device(s) can be used for monitoring the person in two different respects: it is possible not only to ascertain potential movements of the person but also to infer physiological events particularly advantageously and to make suitable use of the events with regard to the magnetic resonance imaging or magnetic resonance data acquisitions.

Thus, a development of an embodiment of the present invention can provide that the controller comprises a trigger unit which, on a trigger criterion being fulfilled, which trigger criterion evaluates the person-related data of the person, in particular verifies the presence of a physiological event, controls the acquisition unit to acquire a magnetic resonance dataset using a magnetic resonance sequence assigned to the trigger criterion. At least one of the magnetic resonance sequences assigned to the at least one trigger criterion can also be one of the at least one prolonged magnetic resonance sequences. It can also be provided that the controller comprises a parameterization unit, which adjusts based upon an evaluation of at least some of the person-related data, an acquisition parameter, in particular a slice position and/or a slice extent and/or a slice orientation, of a magnetic resonance sequence to be performed by the acquisition unit. It is particularly expedient here if the trigger unit when evaluating the trigger criterion, and/or the parameterization unit additionally also evaluates magnetic resonance data acquired by the magnetic resonance apparatus, because this data may also contain indications of physiological events and/or anatomical circumstances inside the person.

Physiological events may include, for example, ischemic events, tachyarrhythmias, ventricular extrasystoles and the like. In this regard, so in particular in the case of sporadically occurring physiological events, it has been found that detecting the events is often more easily possible by way of additional devices, in this case the measuring device(s), compared with detection by way of magnetic resonance acquisitions. The results from these measuring device(s) may for example determine, however, which magnetic resonance sequence is used next, in particular what is meant to be acquired next, and with what examination objective.

For instance in the context of cardiovascular diseases, the person can be monitored for overnight ischemic episodes by suitable measuring device(s), where the trigger unit can initiate an additional morphological and/or functional magnetic resonance data acquisition in order to document the physiological event more precisely. In the example given, for instance morphological imaging could be performed that allows the size of the heart to be determined, for instance to ascertain an enlarged atrium, and/or the aorta diameter to be determined. It is obviously also possible to take account of other characteristic features that arise with an associated disease of the person under examination. Functional imaging in the given example can relate to the left ventricular stroke volume, for instance, and such like. It can thus be stated in general that different physiological events can be modeled by different trigger criteria in order to initiate a magnetic resonance data acquisition relating to specific organs or to general regions under examination, for instance to place the focus of the magnetic resonance data acquisition on the heart or the brain.

Person-related data acquired using measuring device(s) is also suitable for drawing conclusions about suitable acquisition parameters, in particular as part of slice planning. For example, it is possible to deduce from a measured body contour of the person the orientation of the person and/or at least the rough position of various organs, where it is possible to use in particular also algorithms from artificial intelligence and/or machine learning to derive associations in particular also directly with acquisition parameters. In particular in the context of the present invention it is possible to apply what are known as "AutoAlign" techniques to perform slice adjustment prior to a magnetic resonance acquisition.

Moreover, 3D cameras, in particular terahertz cameras, and/or other such sensors ("full body scanners") prove useful in particular with regard to determining a body contour of this type, but also with regard to the tracking of movements of the patient. In this context, other measuring device(s) are also suitable especially for acquiring person-related data, and therefore in a preferred embodiment, the at least one measuring device(s) can also comprise a radar sensor, in particular a synthetic aperture radar, and/or an ultrasound sensor.

Thus while the term "scan while you sleep" can generally be applied to the concept described by the invention, the provision of a trigger unit in the controller adds an adaptive component that makes it possible to depart from a fixed magnetic resonance data acquisition process and in particular to respond also to sporadic events, which are more likely to arise during the longer sleep time, and thus to collect extremely useful additional information about the health condition of the patient. Something of this kind would be ultimately inconceivable for clinical magnetic resonance apparatuses known in the prior art because of their only being available for short times.

While the person is sleeping, in particular during a long total acquisition duration using a magnetic resonance sequence, the person may move, for instance if this person changes their pose on the person support apparatus. Thus it is particularly advantageous in the context of an embodiment of the present invention if the controller comprises a motion unit for motion correction and/or motion cleansing of acquired magnetic resonance datasets. It can be specifically provided in this case that the motion unit is designed to analyze person-related data from a measuring device(s) and/or magnetic resonance data from the magnetic resonance dataset and/or navigator data from a navigator sequence, which navigator data is acquired by the acquisition unit, for the purpose of determining motion information for use in the motion correction and/or the motion cleansing.

Thus, in particular sensor-based measuring device(s), for instance the aforementioned 3D cameras and/or terahertz cameras, radar sensors and/or ultrasound sensors, can be used in order to be able to ascertain movements/changes in pose of the person. It is also conceivable, however, to use navigator sequences, which supply navigator data that typically represents one-dimensional or even two-dimensional projections. The "navigator" can be used, for instance, to track the position of a step-change in contrast inside the patient. Since, however, navigator data cannot normally be acquired simultaneously with other magnetic resonance data, this way of proceeding is less preferable in the context of an embodiment of the present invention.

Nonetheless it should also be mentioned at this point that in principle it would also be conceivable in the context of an embodiment of the present invention to allow navigator data acquired using a navigator sequence to be evaluated, in particular also exclusively, by a trigger criterion (which has already been discussed), although this is something that is less preferred in the context of an embodiment of the present invention because, as already stated, physiological processes, changes and events suitable for the triggering can be ascertained more easily by the additional devices, in this case the measuring device(s), which also are available in a low-cost and compact form.

In addition, motion information can also be derived from the magnetic resonance dataset itself, in particular if large amounts of magnetic resonance data is acquired from a region under examination and retrospective motion correction is meant to be performed. Thus the motion unit of the controller can be designed in particular also for retrospective motion correction.

In this context it is particularly advantageous if the motion unit is designed to delete magnetic resonance data acquired during movement, in particular movement that fulfills a movement intensity criterion, in particular a change in sleeping position, of the person, and/or to merge into a common coordinate system magnetic resonance data from a magnetic resonance dataset, which data has been acquired during different sleeping poses of the person.

In other words, it is particularly advantageous if magnetic resonance data accrued during a movement phase, which usually constitutes only an extremely small proportion of the total acquisition duration, is discarded or disregarded. The number of different poses of the person during such a movement phase is extremely large, and therefore any correction in this regard would be complex and prone to errors. What is more, magnetic resonance data omitted in this way is of little importance in comparison with the extremely long total acquisition duration in the context of the present invention, and therefore there is little or no impact on the quality. A movement intensity criterion, for instance which can stipulate a minimum movement distance and/or a minimum movement speed and/or can distinguish periodic movements such as respiratory movement, can be used to exclude ultra-small movements and normal physiological processes from the omission processes.

As regards merging magnetic resonance data before and after a movement phase, i.e. movement data relating to different sleeping poses, according to a particularly advantageous embodiment of the present invention, the motion unit is designed to use 3D-morphing for the merging. Morphing techniques are already widely known in the prior art and relate to the potential ability to use suitable morphing algorithms to infer from movements at certain sites in a three-dimensional object, in this case in the person, in particular of landmarks, the movement of additional points of the three-dimensional object, in this case of the person. In addition to the morphing algorithms, however, it is obviously also possible in the context of embodiments of the present invention to employ other approaches, for instance general interpolation and/or extrapolation approaches, in order to generate ultimately motion fields, which associate points in one sleeping pose with points in the other sleeping pose and hence allow a corresponding association of pixels.

To summarize, the motion unit can thus be designed to determine at least one movement of the person during the acquisition of a magnetic resonance dataset, in particular using the prolonged magnetic resonance sequence, in particular by analyzing person-related data from at least one measuring device(s). In addition, the motion unit can be designed to delete magnetic resonance data acquired during a movement phase in which the at least one movement takes place and/or to translate into a common coordinate system, based upon the motion information, magnetic resonance data acquired in different sleeping poses of the person. Thus it is possible particularly advantageously to obtain a coherent magnetic resonance dataset as the end result despite the long total acquisition duration.

The field of view of the magnetic resonance apparatus can have a different configuration, in particular dimensions, depending on the target direction. A relatively small field of view can always be sufficient if the magnetic resonance apparatus is meant to be used to monitor or examine only certain regions of the person, for instance the head, by magnetic resonance data acquisition. It can also be expedient, however, if the magnetic resonance apparatus has a field of view of length at least one meter, in particular at least two meters, along the sleeping place. In particular, the field of view can include at least substantially the entire sleeping area of the person support apparatus, or substantially the entire sleeping place. This provides the flexibility to be able to respond to different sleeping poses, and/or, in particular also when using a trigger unit, to select different regions under examination on the person or to obtain magnetic resonance data therefrom. In particular, this exploits the feature of the present invention of working with extremely low main magnetic field strengths, since it is then easier to establish the required homogeneity.

A particularly advantageous further embodiment of the present invention dispenses with providing shielding measures, in particular a shielded cabin. It can be provided specifically in this case that the magnetic resonance apparatus comprises at least one measurement antenna for measuring radiofrequency signals representing radiofrequency interference, and the controller comprises a correction unit for correcting the radiofrequency interference in measured magnetic resonance signals, in particular using a transfer function determined in a calibration process, based upon the radiofrequency signals acquired at the same time instant as the magnetic resonance signals. In particular, it is thus possible to measure potential radiofrequency interference externally by way of additional measurement antennas, and the effects of this radiofrequency interference on the respective radiofrequency coils of the radiofrequency coil arrangement can be known, in particular from a calibration process in which, for instance, a transfer function can be determined. It is then possible, in particular by way of the transfer function, to determine from the radiofrequency signals a correction signal for each radiofrequency coil of the radiofrequency coil arrangement, which correction signal can then be subtracted from the acquired magnetic resonance signal for the purpose of correction in order to correct or eliminate at least some of the radiofrequency interference. Thus by virtue of this and similar procedures it is possible to dispense with a costly shielded cabin and/or other costly shielding measures and yet still be able to perform a largely interference-free magnetic resonance measurement. Reference is made purely by way of example to EP 3 467 531 A1, the entire contents of which are hereby incorporated herein by reference, in regard to known developments in active radiofrequency interference correction by way of additional measurement antennas.

It can also be provided in the context of an embodiment of the present invention that the controller comprises an interface to a personal database, in particular to an electronic patient record, or comprises the personal database, and is designed to enter into the personal database at least some of the acquired magnetic resonance data from the person and/or an analysis result for at least some of the acquired magnetic resonance data from the person. In this case, it can be provided in a particularly advantageous embodiment of the invention that the magnetic resonance datasets in the personal database, in particular the electronic patient record, which datasets are acquired in particular in a plurality of sleeping periods, for instance overnight, can be fused with other health data on the person. The magnetic resonance apparatus according to an embodiment of the invention in particular allows personal health data, i.e. the magnetic resonance datasets, to be collected over the lifetime of a person, and thus to contribute, for example, to creating a "digital twin", since an electronic patient record managed in this way contains a large amount of highly relevant information for assessing the person's health condition. Where measuring device(s) are available, it is possible to enter into the personal database in addition to the magnetic resonance datasets also at least some person-related data from the measuring device(s), in particular associated with the magnetic resonance datasets, something that also applies to analysis results obtained by the controller, for instance the presence of certain physiological events relating to the trigger criteria.

It should also be mentioned at this point that the magnetic resonance datasets need not necessarily be reconstructed image datasets, but it is also conceivable, for example, that just tissue parameters, in particular gradual changes in relaxation times, for instance in the T1 relaxation time, in a body region are determined as the magnetic resonance data of a magnetic resonance dataset. This is expedient in particular when it is necessary to relinquish a high spatial resolution as a result of the low main magnetic field strength.

While the magnetic resonance apparatus according to an embodiment of the invention can be used with particular advantage in a private home, for instance a private apartment or private house, in the context of an embodiment of the present invention it is obviously equally conceivable to use magnetic resonance apparatuses according to the invention in clinics, hotels, homes for the elderly, or suchlike, in particular in order to monitor people, in particular patients, over prolonged time frames during sleeping periods. In other words, the magnetic resonance apparatus can be employed particularly advantageously whenever it is intended to be used by one person continuously over many hours, in particular during the overnight sleep period.

An embodiment of the present invention also relates, in addition to the magnetic resonance apparatus, to a method for operating a magnetic resonance apparatus according to an embodiment of the invention, in which method the at least one prolonged magnetic resonance sequence is used to acquire at least one magnetic resonance dataset from a person sleeping on the sleeping place. All the statements relating to the magnetic resonance apparatus according to an embodiment of the invention can also be applied analogously to the method according to an embodiment of the invention, and therefore the advantages already described can also be achieved by the method. In addition, in particular different functionalities of the controller can also be interpreted as method steps, for instance performing motion correction and/or motion cleansing, and/or triggering specific magnetic resonance sequences or parameterizing the sequences, in particular based upon the person-related data.

It is particularly advantageous in the context of an embodiment of the present invention if the prolonged magnetic resonance sequence is used while the person is in a deep-sleep stage. It is possible to ascertain that the deep-sleep stage is reached, in particular shortly after the person has fallen asleep, for instance by way of measuring device(s) and/or other magnetic resonance data and/or navigator data, where it can be versified, for example, that the person is no longer making deliberate movements or the like. In addition, data on the respiratory and cardiac-cycle behavior of the person can provide clear indications of when the person has fallen asleep and in particular also when the person has entered a deep-sleep stage.

A computer program according to an embodiment of the invention can be loaded, for example, directly into a memory of a controller of a magnetic resonance apparatus according to an embodiment of the invention, and comprises program segments to perform the steps of a method according to the invention when the computer program is executed in the controller of the magnetic resonance apparatus. The computer program can be stored on an electronically readable data storage medium according to an embodiment of the invention, which therefore comprises electronically readable control information stored thereon that comprises at least one the computer program and is designed such that it performs a method according to an embodiment of the invention when the data storage medium is used in a controller of a magnetic resonance apparatus according to an embodiment of the invention. The data storage medium may be in particular a non-transient data storage medium, for instance a CD-ROM.

FIG. 1 shows a schematic diagram of fundamental components of a magnetic resonance apparatus 1 according to an embodiment of the invention. In general terms, this uses a main magnetic field of strength less than 20 mT, preferably less than 10 mT. The magnetic resonance apparatus 1 comprises a person support apparatus 2, which is designed to form a sleeping place for the person. For this purpose, the person support apparatus 2 comprises in particular a mattress and/or a blanket and/or a pillow. In addition, an acquisition arrangement 3 comprising at least one radiofrequency coil arrangement 4 is provided for acquiring magnetic resonance data. The radiofrequency coil arrangement 4 comprises at least one, although usually more than one, radiofrequency coil, of which at least some, in particular all, can be integrated in the person support apparatus 2. For instance it is conceivable to integrate in the mattress, a mattress protector, the blanket and/or the pillow, radiofrequency coils of the radiofrequency coil arrangement 4, which are in the form of local coils or local-coil elements. It is also possible, however, to incorporate radiofrequency coils in items of clothing that can be worn by the person.

As an optional component, the acquisition arrangement 3 can also comprise a main-field generating apparatus 5, unless the intention is to work solely with the Earth's magnetic field as the main magnetic field. The main-magnetic-field generating apparatus preferably comprises at least one main field coil, for instance one Helmholtz coil or a pair of Helmholtz coils. It is also conceivable for the main-field generating apparatus to comprise at least one permanent magnet. The low main magnetic field strengths mean that there is no need for superconduction. In addition, the optional main-field generating apparatus 5 can preferably be integrated in the person support apparatus 2.

If the magnetic resonance apparatus 1 is meant to use, possibly solely, the Earth's magnetic field as the main magnetic field, the acquisition arrangement 3 can optionally and preferably comprise a pre-polarization apparatus 6, which likewise can comprise at least one pre-polarization coil in the form of an electromagnet, and which is used in the Earth's magnetic field in a generally known manner to pre-polarize the nuclear spins of the person to be scanned. The pre-polarization apparatus 6 can also preferably be integrated in the person support apparatus 2.

Finally, it is also conceivable as an option that the acquisition arrangement 3 comprises a gradient coil arrangement 7 containing at least one gradient coil, which is used for spatial encoding by way of gradients of the main magnetic field. In the context of an embodiment of the present invention, however, it is preferred to produce the spatial encoding by way of the radiofrequency coils of the radiofrequency coil arrangement 4. Moreover, it is entirely conceivable in this case that radiofrequency coils of the radiofrequency coil arrangement 4 are operated not only as a transmit and/or receive coil but also with regard to the spatial encoding, for instance using the TRASE method.

The magnetic resonance apparatus 1 is controlled by a controller 8, which can be integrated at least in part in the person support apparatus 2, as also can at least one gradient coil of the gradient coil arrangement 7, if present. The controller 8 is at least designed to acquire a magnetic resonance dataset from a person sleeping on the sleeping place of the person support apparatus 2 using a prolonged magnetic resonance sequence of total acquisition duration longer than one hour and in particular containing more than 1000 repetitions. The long total acquisition duration at least partially offsets the loss in signal-to-noise ratio resulting from the low main magnetic field strength. The controller 8 is obviously also designed to use other magnetic resonance sequences, in particular of a shorter total acquisition duration, to acquire magnetic resonance datasets, although again in this case significantly longer total acquisition durations than normal may exist, for instance total acquisition durations longer by a factor of 100 than in comparable clinical devices, in particular total acquisition durations that are longer than 10 minutes, in particular longer than 30 minutes. In addition, navigator sequences for acquiring navigator data can be used in the controller 8, and in the case that a pre-polarization apparatus 6 is provided, each magnetic resonance sequence that is meant to use the Earth's magnetic field expediently comprises pre-polarization pulses.

If a gradient coil arrangement 7 is used, the controller 8 is designed such that in at least one magnetic resonance sequence used, in particular the at least one prolonged magnetic resonance sequence, it switches gradients only before each excitation pulse but not between excitation and readout period or during the readout period that follows the associated excitation pulse. Radial sampling of k-space is particularly suitable in this case. The switching of gradients solely outside an excitation pulse succeeded by readout period provides a longer time frame for the switching process, and therefore the controller 8 is designed in this case to use gradient switching times that are longer than 1 ms, in particular longer than 10 ms. By virtue of the low main magnetic field strength, low gradient strengths are already sufficient, in this case gradient strengths of less than 1 mT/m, in particular less than 200 µT/m.

It is particularly preferred in the magnetic resonance apparatuses 1 according to an embodiment of the invention, however, as already mentioned, to omit the gradient coil arrangement 7 entirely and to achieve the spatial encoding by way of the radiofrequency coil arrangement 4. In this case, when controlling the radiofrequency coil arrangement 4, the controller 8 can employ, for example, the TRASE method and/or a Bloch-Siegert shift gradient for the purpose of spatial encoding.

The magnetic resonance apparatus 1 can also optionally and preferably comprise at least one measuring device(s) 9 for determining person-related data of a person sleeping on the sleeping place. The person-related data may describe physiological processes inside the person and/or the movement behavior of the person. Measuring device(s) 9 that are suitable in this context are in particular a 3D camera, in particular in the form of a terahertz camera, an ECG apparatus, a heart rate monitor, an oximeter, at least one radar sensor and/or at least one ultrasound sensor. Using a terahertz camera makes it possible in particular to detect the surface contour of the person even through a blanket or the like. In addition, other forms of scan apparatuses of this type, for instance "full body scanners", can also be used as the measuring device(s) if the person is covered during sleeping. The person-related data from the measuring device(s) 9 is also analyzed by the controller 8 in the manner described in greater detail below.

The magnetic resonance apparatus 1 comprises likewise optionally and preferably at least one measurement antenna 10 in order to acquire radiofrequency signals representing radiofrequency interference, which signals can be used by the controller 8 to correct magnetic resonance signals acquired by the radiofrequency coil arrangement 4. The magnetic resonance apparatus 1 thereby does not need a shielded cabin and/or other additional shielding measures, and thus these are also not provided.

Figure 2:
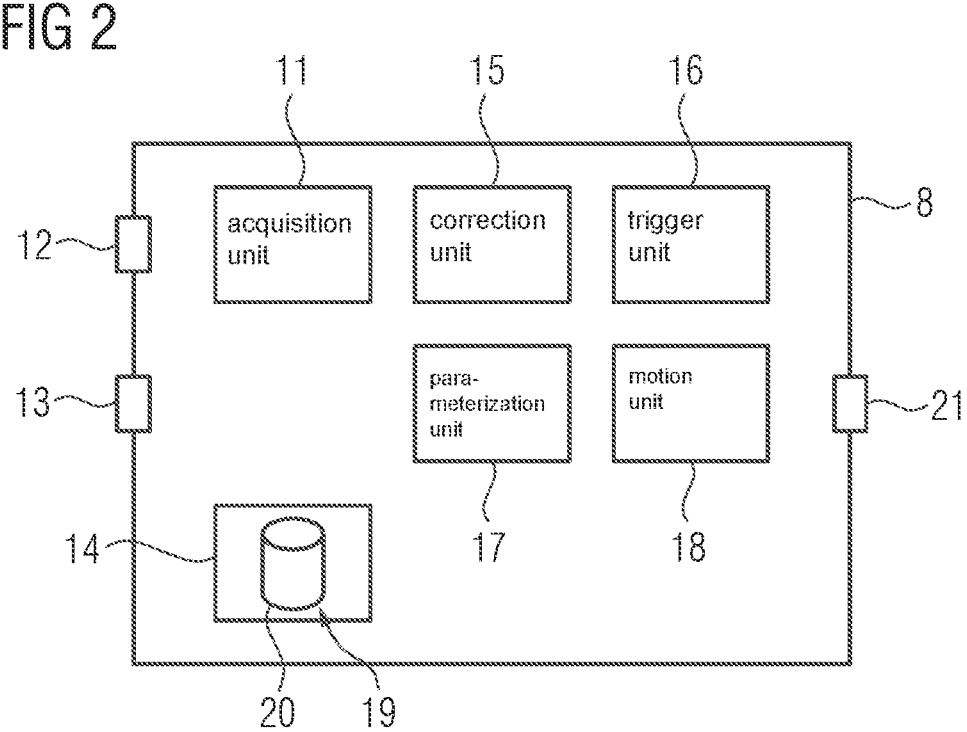
FIG. 2 shows the functional design of a controller of a magnetic resonance apparatus according to an embodiment of the invention.

FIG. 2 shows the functional design of the controller 8 in greater detail. First this comprises, as generally known, an acquisition unit 11, which is used to control the acquisition arrangement 3 in accordance with a magnetic resonance sequence, in particular at least occasionally also in accordance with the prolonged magnetic resonance sequence, in order to acquire magnetic resonance datasets for the person sleeping on the sleeping place. The acquisition arrangement 3 (and other components of the magnetic resonance apparatus 1) are controlled via a corresponding interface 12. A further interface 13 receives data, in particular from the at least one measuring device(s) 9 and/or from the at least one measurement antenna 10, which data is used in further functional units explained in greater detail. Magnetic resonance sequences can be stored, for example, in a storage device(s) 14 of the controller 8. It should be mentioned that the acquisition unit 11 and, if applicable, further functional units can be implemented in particular by at least one processor of the controller 8 (not shown) in conjunction with program segments, which in particular also include program segments of a computer program according to an embodiment of the invention.

As a further functional unit, the controller 8 comprises a correction unit 15, which uses a transfer function to convert the radiofrequency signals from the measurement antennas 10 into correction signals, which are subtracted from measured magnetic resonance signals. In particular, the radiofrequency signals that were acquired simultaneously with the magnetic resonance signals are used in this case.

A trigger unit 16, a parameterization unit 17 and a motion unit 18 all use person-related data from the at least one measuring device(s) 9. In addition, these functional units 16-18 can also analyze pre-acquired magnetic resonance data of the person and navigator data from a navigator sequence. In this case the trigger unit 16 checks by analyzing the person-related data and, if applicable, also magnetic resonance data and/or navigator data, whether one of a plurality of trigger criteria, each assigned to a particular magnetic resonance sequence, is fulfilled. The trigger criteria verify whether a specific physiological event exists, for instance an extrasystole occurrence, an ischemic episode, breath-holding or the like. In particular, monitoring for sporadically occurring physiological events is performed here, since the likelihood of an occurrence during a long sleep period of the person is significantly higher than in a short-term examination in standard clinical equipment using a high field. Suitable magnetic resonance sequences are assigned to each of the trigger criteria for the purpose of more precise examination and documentation of the physiological event, and these sequences are selected and performed on the trigger criterion being fulfilled, in order to collect the relevant additional magnetic resonance information. For instance, magnetic resonance datasets for the heart can be acquired in the event of heart irregularities. The magnetic resonance sequences assigned to the trigger events include in particular also at least one prolonged magnetic resonance sequence.

In the parameterization unit 17, the person-related data from the at least one measuring device(s) 9 is analyzed in order to select acquisition parameters for a magnetic resonance sequence to be performed at that time, in particular also the prolonged magnetic resonance sequence, which parameters are suitably adjusted to the current condition of the person, in particular their sleeping pose. Thus it is possible to determine in particular a current sleeping pose of the person, for example from person-related data from the 3D terahertz camera and/or from the radar sensor and/or the ultrasound sensor, and to infer from the contour of the person also the position of internal points, in particular of organs. Patient models, for instance, can be used for this purpose, which can also be based at least in part on artificial intelligence and/or machine learning. Slice parameters, in particular a slice position and/or a slice extent and/or a slice orientation, can then be suitably adjusted, for instance in the manner of an "AutoAlign" method, based upon the results of this analysis.

Finally, the motion unit 18 is designed for motion correction and motion cleansing of acquired magnetic resonance datasets. This process involves checking by way of the person-related data from the at least one measuring device(s) 9 and/or from navigator data and/or retrospectively by analyzing the magnetic resonance data from the magnetic resonance dataset in particular whether the person has changed sleeping pose during the total acquisition duration. If this is the case, the magnetic resonance data is ultimately divided into different data blocks, namely magnetic resonance data acquired during respective sleeping poses, and magnetic resonance data acquired in the movement stage in which the change takes place from the one sleeping pose into the other sleeping pose. The latter magnetic resonance data is discarded in order to cleanse the magnetic resonance dataset. Merging into a common coordinate system, in particular using 3D-morphing, is performed for magnetic resonance data from different sleeping poses. It is thereby possible to assemble consistent magnetic resonance datasets containing maximum possible magnetic resonance data despite the long total acquisition duration and the possible change in sleeping poses.

An electronic patient record 20 of the person can be stored as the personal database 19 in the storage apparatus 14 of the controller 8, and/or the controller 8 can comprise an interface 21 to an external processing apparatus in which the personal database 19 exists. The controller 8 then ensures that current magnetic resonance datasets and/or analysis results from current magnetic resonance datasets, if applicable together with person-related data and/or analysis results from person-related data, are added to the electronic patient record 20 in order to contribute to creating a "digital twin". It is thereby possible to collect personal health data over the person's lifetime. It should be mentioned at this point that the magnetic resonance datasets need not necessarily contain reconstructed magnetic resonance images, but also, for instance in parts, may also describe parameters and/or parameter changes, for example relating to a relaxation time.

Figure 3:
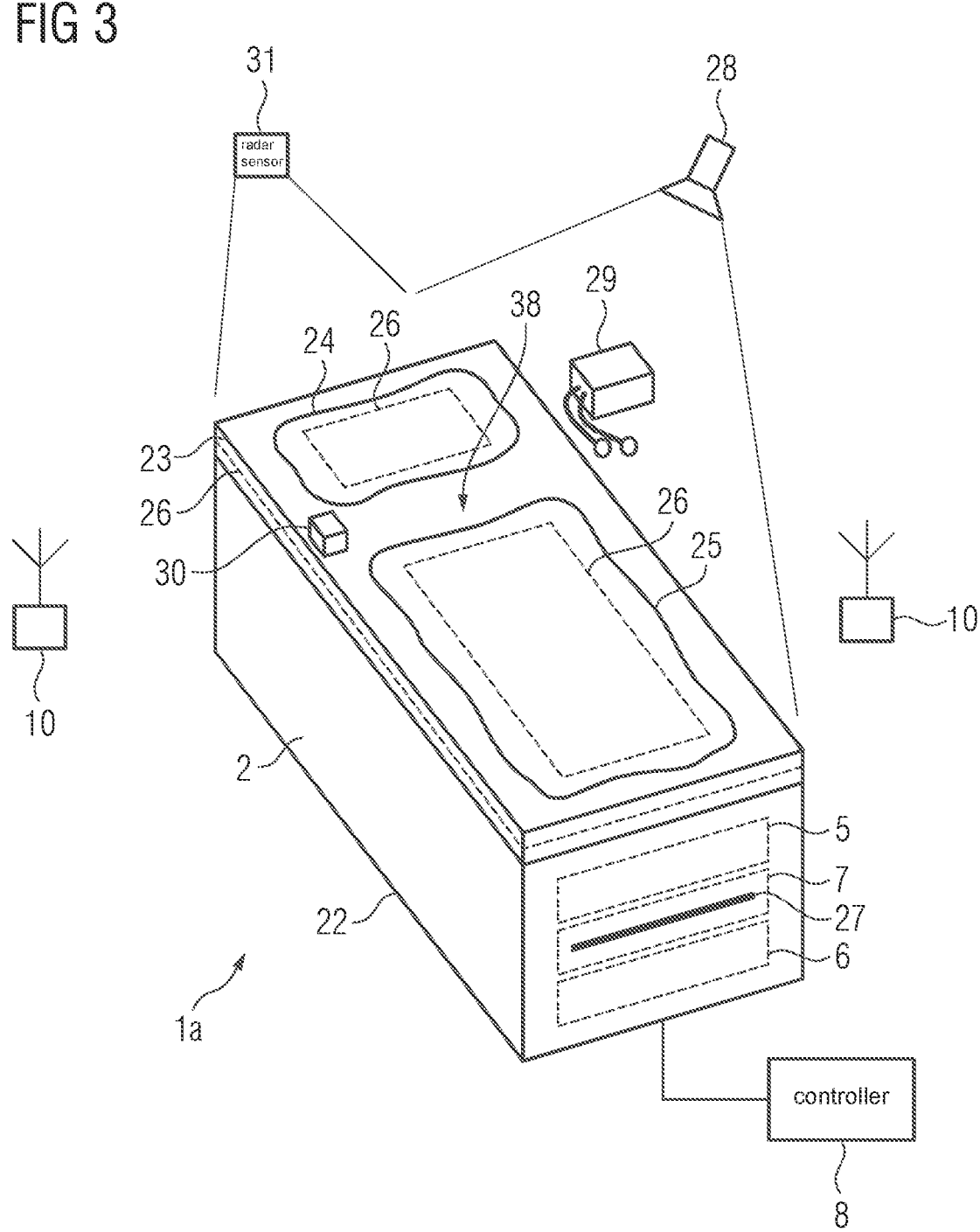
FIG. 3 shows a first specific example embodiment of a magnetic resonance apparatus according to the invention.

FIG. 3 shows a first specific example embodiment of a magnetic resonance apparatus 1a according to the invention. It shows the person support apparatus 2 in the form of a compact bed that is substantially cuboid in shape and comprises, in addition to a base element 22, a mattress 23, which is arranged on the base element 22 and provides the sleeping place, a pillow 24 and a blanket 25. Radiofrequency coils 26 (merely intimated in each case) of the radiofrequency coil arrangement 4 are integrated in the mattress 23, the pillow 24 and the blanket 25. The optional main-field generating apparatus 5, the optional gradient coil arrangement 7 and/or the optional pre-polarization apparatus 6 can be integrated in the base element 22. If a gradient coil arrangement 7 is used, then the at least one, in particular precisely one, gradient coil 27 is a mono-planar, flat gradient coil, and the controller 8 is designed to use suitable generally known methods to correct gradient non-linearities. The flat design of the gradient coil 27 means that it can be integrated particularly easily in the base element 22.

It should be pointed out that parts of the controller 8 can also be integrated in the base element 22, and therefore the magnetic resonance apparatus 1a can also be called a magnetic resonance bed.

Like the measurement antennas 10, at least some of the measuring device(s) 9 can also be spaced apart from, or independent of, the person support apparatus 2. In the present case, the measuring device(s) 9 comprises by way of example a 3D terahertz camera 28, an ECG apparatus 29, a combined heart-rate monitor/oximeter 30 and a radar sensor 31. Since no other components of the acquisition arrangement 3 are needed above the sleeping place 38 provided by the mattress 23, a particularly open field of view is obtained for the camera 28 and the radar sensor 31, where preferably a plurality of radar sensors 31 are provided.

Figure 4:
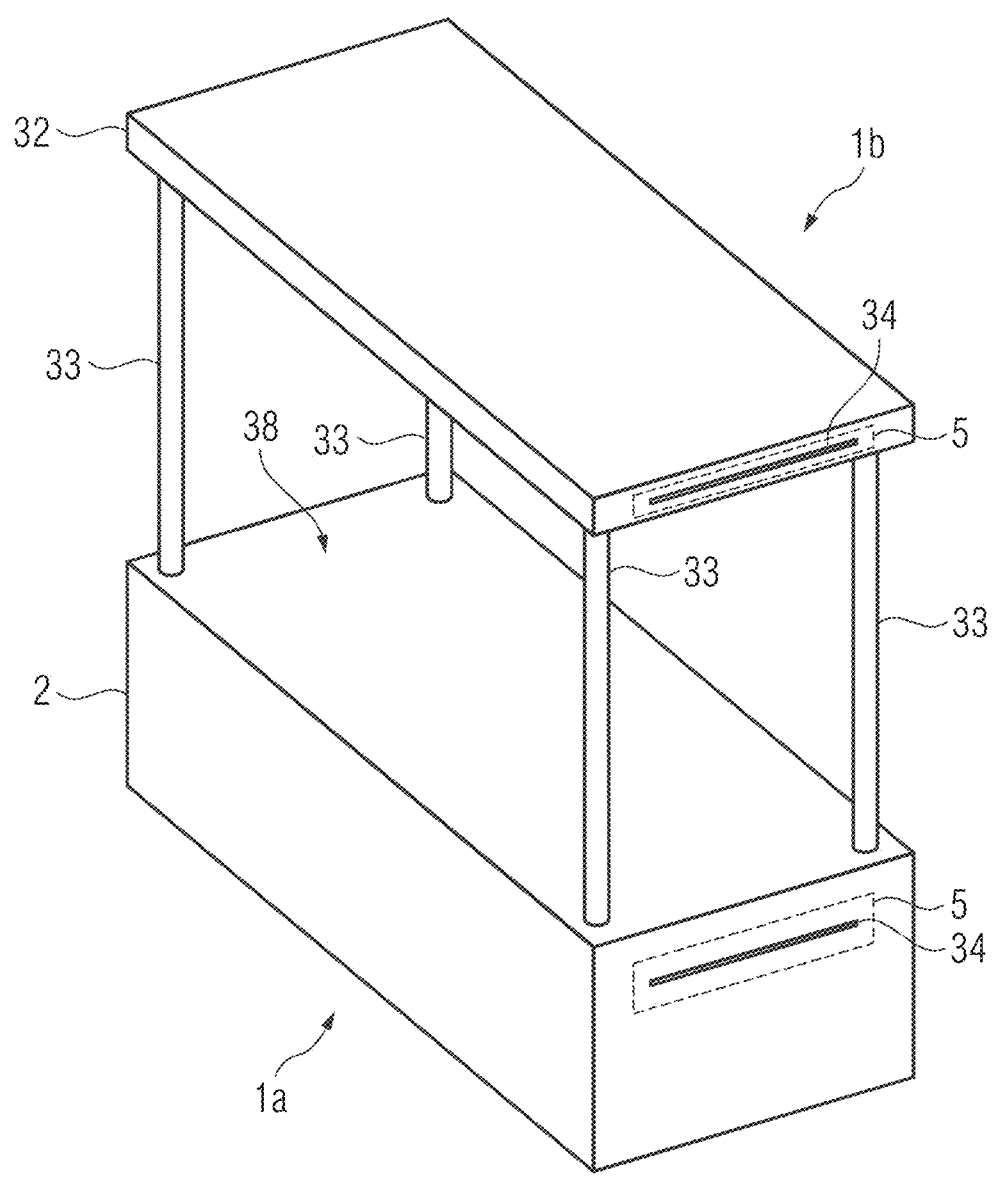
FIG. 4 shows a second specific example embodiment of a magnetic resonance apparatus according to the invention.

FIG. 4 shows a second example embodiment of a magnetic resonance apparatus 1b according to the invention, and, for the sake of simplicity, shows only those parts that differ from the magnetic resonance apparatus 1a. In the case shown here, the person support apparatus 2 thus comprises four posts 33 bearing a support 32 in the manner of a four-poster bed, which allows, for example, parts of the acquisition arrangement 3 to be provided also in the support 32 or even in the posts 33, although the narrow posts 33 mean it is possible to retain a good field of view for the 3D terahertz camera 28, the radar sensor 31 and the like. FIG. 4 shows purely by way of example that the optional main-field generating apparatus 5 is distributed between two coils of a Helmholtz-coil pair 34.

Figure 5:
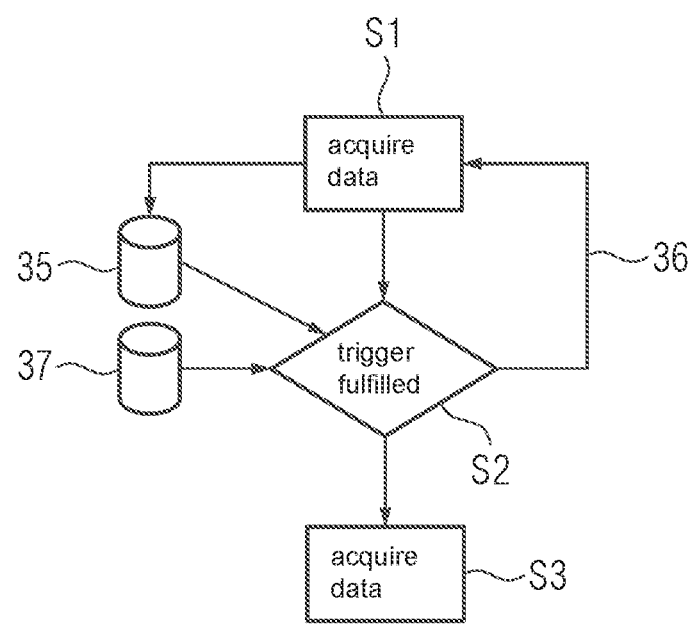
FIG. 5 shows a flow diagram for the triggered magnetic resonance data acquisition during sleep.

FIG. 5 shows a flow diagram for explaining in greater detail the operation of the trigger unit 16. A normal acquisition and/or monitoring operation, defined previously without particular physiological events, takes place in a step S1. In this step, magnetic resonance datasets 35 for the person may already be produced, for instance using the prolonged magnetic resonance sequence.

According to a step S2, the trigger unit 16 regularly or continuously monitors for potential fulfillment of trigger criteria. If no trigger criterion is fulfilled, the acquisition and/or monitoring operation of step S1 continues, as shown by the arrow 36. With regard to checking fulfillment of a trigger criterion, as already described, person-related data 37 from the measuring device(s) 9 is evaluated in all cases, with the option to use also magnetic resonance data from already acquired magnetic resonance datasets 35 or from magnetic resonance datasets 35 in the process of being acquired.

If a trigger criterion is fulfilled in step S2, then in a step S3, magnetic resonance data acquisition continues using the magnetic resonance sequence assigned to the trigger criterion.

To conclude, it should be mentioned that the controller of the magnetic resonance apparatus 1, 1a, 1b according to an embodiment of the invention can also be designed to use arterial spin labeling. This can provide a substitute for a contrast agent, in particular for both morphological and functional magnetic resonance imaging.

Although the invention has been illustrated and described in detail using the preferred example embodiment, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A magnetic resonance apparatus for acquiring magnetic resonance data from a person who is asleep, comprising:
   a person support apparatus, to provide a sleeping place;
   an acquisition arrangement, including a radiofrequency coil arrangement to transmit excitation pulses and to receive magnetic resonance signals; and
   a controller, designed to operate the acquisition arrangement according to a magnetic resonance sequence for acquiring a magnetic resonance dataset from a region under examination of the person, and the controller including:
      an acquisition unit to acquire a magnetic resonance dataset by way of a single uninterrupted magnetic resonance sequence having a total acquisition duration of more than one hour, wherein the magnetic resonance apparatus has a main magnetic field of strength less than 20 mT.

2. The magnetic resonance apparatus of claim 1, wherein at least one of
the prolonged magnetic resonance sequence includes more than 1000 repetitions and
the controller is designed to use arterial spin labeling as a contrast-agent substitute.

3. A magnetic resonance apparatus for acquiring magnetic resonance data from a person who is asleep, comprising:
a person support apparatus, to provide a sleeping place;
an acquisition arrangement, including a radiofrequency coil arrangement to transmit excitation pulses and to receive magnetic resonance signals; and
a controller, designed to operate the acquisition arrangement according to a magnetic resonance sequence for acquiring a magnetic resonance dataset from a region under examination of the person, and the controller including:
an acquisition unit to acquire a magnetic resonance dataset by way of a prolonged magnetic resonance sequence having a total acquisition duration of more than one hour, where the magnetic resonance apparatus has a main magnetic field of strength less than 20 mT, wherein the magnetic resonance apparatus is designed to use the Earth's magnetic field as the main magnetic field, and
wherein at least one of
a pre-polarization apparatus for aligning nuclear spins of the person before a measurement is provided as part of the acquisition arrangement, and
the magnetic resonance apparatus includes, as part of the acquisition arrangement, a main-field generating apparatus for generating the main magnetic field.

4. The magnetic resonance apparatus of claim 1, wherein the controller is designed to switch a gradient before an excitation pulse in at least one magnetic resonance sequence used.

5. The magnetic resonance apparatus of claim 1, wherein the controller is designed to use the radiofrequency coil arrangement to spatially encode in the magnetic resonance data acquisition.

6. A magnetic resonance apparatus for acquiring magnetic resonance data from a person who is asleep, comprising:
a person support apparatus, to provide a sleeping place;
an acquisition arrangement, including a radiofrequency coil arrangement to transmit excitation pulses and to receive magnetic resonance signals; and
a controller, designed to operate the acquisition arrangement according to a magnetic resonance sequence for acquiring a magnetic resonance dataset from a region under examination of the person, and the controller including:
an acquisition unit to acquire a magnetic resonance dataset by way of a prolonged magnetic resonance sequence having a total acquisition duration of more than one hour,
where the magnetic resonance apparatus has a main magnetic field of strength less than 20 mT, and wherein as part of the acquisition arrangement, a flat gradient coil of a gradient coil arrangement, arranged only on one side of the person support apparatus.

7. The magnetic resonance apparatus of claim 1, wherein at least one radiofrequency coil of the radiofrequency coil arrangement is arranged inside the person support apparatus.

8. The magnetic resonance apparatus of claim 6, wherein the magnetic resonance apparatus is designed to use the Earth's magnetic field as the main magnetic field, and wherein at least one of
a pre-polarization apparatus for aligning nuclear spins of the person before a measurement is provided as part of the acquisition arrangement, and
the magnetic resonance apparatus includes, as part of the acquisition arrangement, a main-field generating apparatus for generating the main magnetic field, and
wherein, in addition to the gradient coil and the at least one radiofrequency coil, at least one of the main-field generating apparatus and the pre-polarization apparatus are also integrated in the person support apparatus.

9. The magnetic resonance apparatus of claim 1, further comprising:
at least one additional measuring device, to acquire person-related data of the person.

10. The magnetic resonance apparatus of claim 9, wherein the at least one measuring device includes at least one of
a camera,
an ECG apparatus,
a heart rate monitor,
an oximeter,
a radar sensor, and
an ultrasound sensor.

11. The magnetic resonance apparatus of claim 9, wherein at least one of
the controller includes a trigger unit which, upon a trigger criterion being fulfilled, the trigger criterion evaluating person-related data of the person, is configured to control the acquisition unit to acquire a magnetic resonance dataset using a magnetic resonance sequence assigned to the trigger criterion, and
the controller includes a parameterization unit to adjust, based upon an evaluation of at least some of the person-related data, an acquisition parameter of a magnetic resonance sequence to be performed by the acquisition unit.

12. The magnetic resonance apparatus of claim 9, wherein the controller includes a motion unit to at least one of motion correct and motion cleanse acquired magnetic resonance datasets.

13. The magnetic resonance apparatus of claim 12, wherein the motion unit is designed to analyze at least one of person-related data from the measuring device, magnetic resonance data from the magnetic resonance dataset, and navigator data from a navigator sequence, the navigator data being acquired by the acquisition unit for a purpose of determining motion information for use in at least one of the motion correction and the motion cleansing.

14. The magnetic resonance apparatus of claim 13, wherein the motion unit is designed to delete magnetic resonance data acquired during movement.

15. The magnetic resonance apparatus of claim 1, wherein the magnetic resonance apparatus includes a field of view of length at least one meter, along a sleeping place.

16. The magnetic resonance apparatus of claim 1, further comprising:
at least one measurement antenna to measure radiofrequency signals representing radiofrequency interference, wherein the controller includes a correction unit to correct the radiofrequency interference in measured magnetic resonance signals, based upon the radiofrequency signals acquired at a same time instant as the magnetic resonance signals.

17. The magnetic resonance apparatus of claim 1, wherein the controller includes an interface to a personal database, or comprises the personal database, and is designed to enter into the personal database at least one of at least some of the acquired magnetic resonance data from the person and an analysis result for at least some of the acquired magnetic resonance data from the person.

18. A method for operating a magnetic resonance apparatus including a person support apparatus, to provide a sleeping place; an acquisition arrangement, including a radiofrequency coil arrangement to transmit excitation pulses and to receive magnetic resonance signals; and a controller, designed to operate the acquisition arrangement according to a magnetic resonance sequence for acquiring a magnetic resonance dataset from a region under examination of the person, and the controller including an acquisition unit to acquire a magnetic resonance dataset by way of a single uninterrupted magnetic resonance sequence having a total acquisition duration of more than one hour, wherein the magnetic resonance apparatus has a main magnetic field of strength less than 20 mT, the method comprising:
   using at least one prolonged magnetic resonance sequence to acquire at least one magnetic resonance dataset from the person sleeping on the sleeping place of the person support apparatus.

19. A non-transitory computer readable medium storing a computer program, to perform the method of claim 18 when the computer program is executed in a controller of a magnetic resonance apparatus.

20. The magnetic resonance apparatus of claim 1, wherein the main magnetic field strength of the magnetic resonance apparatus is less than 10 mT.

21. A magnetic resonance apparatus for acquiring magnetic resonance data from a person who is asleep, comprising:
   a person support apparatus, to provide a sleeping place;
   an acquisition arrangement, including a radiofrequency coil arrangement to transmit excitation pulses and to receive magnetic resonance signals; and
   a controller, designed to operate the acquisition arrangement according to a magnetic resonance sequence for acquiring a magnetic resonance dataset from a region under examination of the person, and the controller including:
      an acquisition unit to acquire a magnetic resonance dataset by way of a prolonged magnetic resonance sequence having a total acquisition duration of more than one hour, where the magnetic resonance apparatus has a main magnetic field of strength less than 20 mT, wherein the magnetic resonance apparatus is designed to use the Earth's magnetic field as the main magnetic field, and wherein at least one of
      a pre-polarization apparatus for aligning nuclear spins of the person before a measurement is provided as part of the acquisition arrangement, and
      the magnetic resonance apparatus includes, as part of the acquisition arrangement, a main-field generating apparatus for generating the main magnetic field, and wherein the main-field generating apparatus is arranged only on one side of the person support apparatus.

22. The magnetic resonance apparatus of claim 21, wherein the main-field generating apparatus at least one of
   is arranged beneath the sleeping place, and
   includes a Helmholtz-coil pair.

23. The magnetic resonance apparatus of claim 4, wherein the controller is designed to switch a gradient before an excitation pulse is used in at least one prolonged magnetic resonance sequence in which at least one of
   the magnetic resonance sequence includes no further gradient pulses before an end of a readout period following the excitation pulse, and
   the magnetic resonance sequence is designed for radial sampling of k-space.

24. The magnetic resonance apparatus of claim 5, wherein the controller is designed to at least one of
   use at least one of a TRASE method and a Bloch-Siegert shift gradient, and
   use, when a gradient coil is employed, at least one of gradient switching times longer than 1 ms and gradient strengths of less than 1 mT/m.

25. The magnetic resonance apparatus of claim 7, wherein at least one radiofrequency coil of the radiofrequency coil arrangement is arranged inside at least one of
   a mattress on the patient support,
   a pillow on the patient support,
   a blanket on the patient support, and
   an item of clothing wearable by the person.

26. The magnetic resonance apparatus of claim 1, wherein the controller includes a motion unit to at least one of motion correct and motion cleanse acquired magnetic resonance datasets.

* * * * *